(12) United States Patent
Gabet Hoffmeister et al.

(10) Patent No.: US 11,079,287 B1
(45) Date of Patent: Aug. 3, 2021

(54) TEMPERATURE DEPENDENT X-RAY FLUORESCENCE

(71) Applicants: National Technology & Engineering Solutions of Sandia, LLC, Albuquerque, NM (US); Steven F. Son, West Lafayette, IN (US); Eric R. Westphal, West Lafayette, IN (US)

(72) Inventors: Kathryn N. Gabet Hoffmeister, Albuquerque, NM (US); Enrico C. Quintana, Albuquerque, NM (US); Walter Gill, Albuquerque, NM (US); Steven F. Son, West Lafayette, IN (US); Eric R. Westphal, West Lafayette, IN (US)

(73) Assignees: National Technology & Engineering Solutions of Sandia, LLC, Albuquerque, NM (US); Purdue Research Foundation, West Lafayette, IN (US)

(*) Notice: Subject to any disclaimer, the term of this patent is extended or adjusted under 35 U.S.C. 154(b) by 123 days.

(21) Appl. No.: 16/662,669

(22) Filed: Oct. 24, 2019

(51) Int. Cl.
*G01K 11/30* (2006.01)
*G01N 23/223* (2006.01)

(52) U.S. Cl.
CPC .......... *G01K 11/30* (2013.01); *G01N 23/223* (2013.01); *G01N 2223/40* (2013.01)

(58) Field of Classification Search
CPC ...... G01K 11/30; G01N 23/22; G01N 23/223; G01N 2223/40; G01N 2223/076
See application file for complete search history.

(56) References Cited

U.S. PATENT DOCUMENTS 5,272,340 A * 12/1993 Anbar ................... G01J 3/32
250/330

* cited by examiner

*Primary Examiner* — Jurie Yun
(74) *Attorney, Agent, or Firm* — Yee & Associates, P.C.

(57) ABSTRACT

A method and system for determining temperature are provided. The method comprises using an x-ray source to irradiate a sample of a material with x-rays. Photon fluorescence produced by the sample in response to the x-ray irradiation is detected by a number of photon detectors. Based on the detected fluorescence a temperature of the sample is determined according to a predetermined relationship between photon fluorescence and temperature for the material.

21 Claims, 5 Drawing Sheets

TEMPERATURE DEPENDENT X-RAY FLUORESCENCE

STATEMENT OF GOVERNMENT INTEREST

This invention was made with United States Government support under Contract No. DE-NA0003525 between National Technology & Engineering Solutions of Sandia, LLC and the United States Department of Energy. The United States Government has certain rights in this invention.

BACKGROUND

1. Field

The disclosure relates generally to temperature sensing, and more specifically to determining temperature according to x-ray fluorescence of materials.

2. Description of the Related Art

Many manufacturing and testing processes involve materials contained in sealed and optically opaque environments. In such an environment access for wires is challenging, making temperature detection through direct physical contact impractical. Therefore, many current approaches operate with only limited knowledge of the internal behavior.

Figure 6:
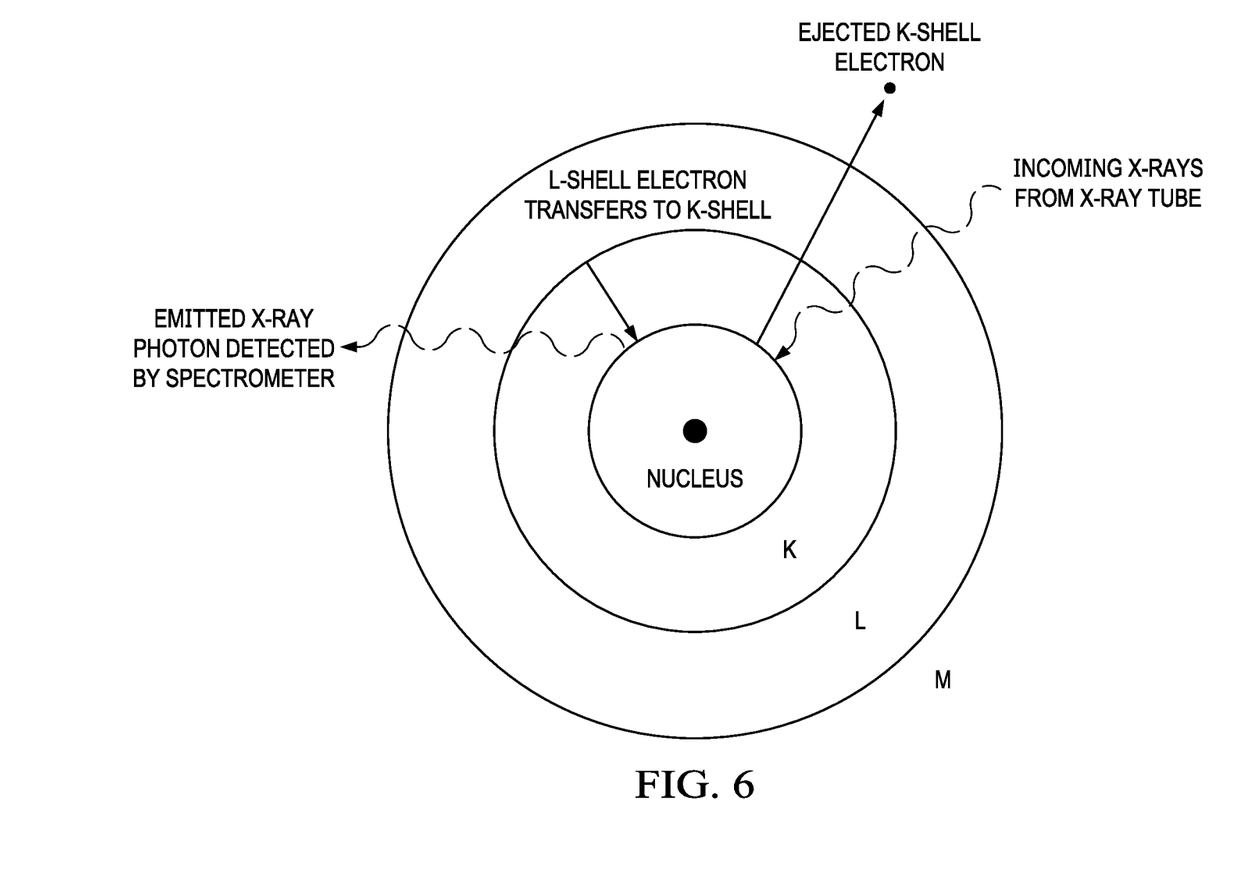
FIG. 6 depicts a visual representation of an atom emitting an x-ray photon in response to x-ray irradiation.

When an x-ray or other ionizing quantum is absorbed into a material, a nonequilibrium state is created. This high-energy quantum has enough energy to create a primary hole in the K-shell of an atom by knocking out a primary electron as shown in FIG. 6. This electron is likely to contact other atoms in the crystal and transfer energy, thereby exciting their electrons. This process is repeated, cascading energy toward lower states and a new equilibrium through the creation of a series of lower energy hole-electron pairs, x-ray fluorescence, UV fluorescence, phonons, visible fluorescence/phosphorescence, and other thermal loses.

The energies of the characteristic x-ray emission lines are determined by a material's elemental make-up. The relative strength of these lines is assumed to be dependent on the mass fraction of a given element and experimental parameters. Characteristic x-ray fluorescence lines in some materials are temperature dependent. Wireless temperature monitoring can enable improvements in manufacturing by enabling feedback control based on knowledge of the internal states. X-ray fluorescence-based techniques are a particularly promising method for wirelessly monitoring temperature.

SUMMARY

An illustrative embodiment provides a method of determining temperature. The method comprises using an x-ray source to irradiate a sample of a material with x-rays. Photon fluorescence produced by the sample in response to the x-ray irradiation is detected by a number of photon detectors. Based on the detected fluorescence a temperature of the sample is determined according to a predetermined relationship between photon fluorescence and temperature for the material.

Another illustrative embodiment provides a system for determining temperature. The system comprises an x-ray source, a number of photon detectors, and a number of processors in communication with the x-ray source and photon detectors, wherein the number of processors are configured to execute program instructions to: irradiate, with the x-ray source, a sample of a material; detect, with the photon detectors, photon fluorescence produced by the sample in response to the x-ray irradiation; and determining a temperature of the sample according to a predetermined relationship between photon fluorescence and temperature for the material.

DETAILED DESCRIPTION

The illustrative embodiments recognize and take into account one or more different considerations. For example, the illustrative embodiments recognize and take into account that many manufacturing and testing processes involve materials contained in sealed and/or optically opaque environments that do not allow access for direct temperature detection. These opaque environments might include containers in which the material sample is enclosed. Another example is a sooty fire in which the sample is location, e.g., steel mill furnace.

Alternatively, the sample itself might be opaque, preventing measurement of the interior temperature of the sample, which is necessary in order to determine average temperature rather than just the exterior/surface temperature. Examples of opaque samples include plasma sprays, burning rocket propellant, explosives, nuclear fuel rods, and metal beams.

Illustrative embodiments also recognize and take into account that characteristic x-ray fluorescence lines in some materials are temperature dependent.

Illustrative embodiments provide a method of temperature diagnostics capable of noncontact measurements in optically obscured environments. Changes in x-ray emission lines are measured, and the ratio of the emissive line strength is used to measure the material's temperature. This is analogous to the way thermographic phosphors are used to measure temperature in the visible spectrum. As such, the time decay of these characteristic x-ray emission lines after x-ray/gamma-ray/electron excitation are temperature dependent.

Excitation of thermographic materials causes these materials to fluoresce. The typical excitation source for these materials are lasers (and even LEDs). During laser excitation, atoms undergo electronic energy level transitions involving their valence electrons. These transitions lead to the production of photons with energies primarily within the visible region. In contrast, x-ray excitation penetrates further within the atoms to core electrons. The resulting electronic energy level transitions would produce photons within the x-ray region. Use of an x-ray source for excitation in certain environments allows for simultaneous x-ray probing and temperature measurement of a sample.

Illustrative embodiments reduce the physical modifications currently necessary when measuring inside objects or in optically-dense environments with other techniques, such as thermocouples.

Figure 1:
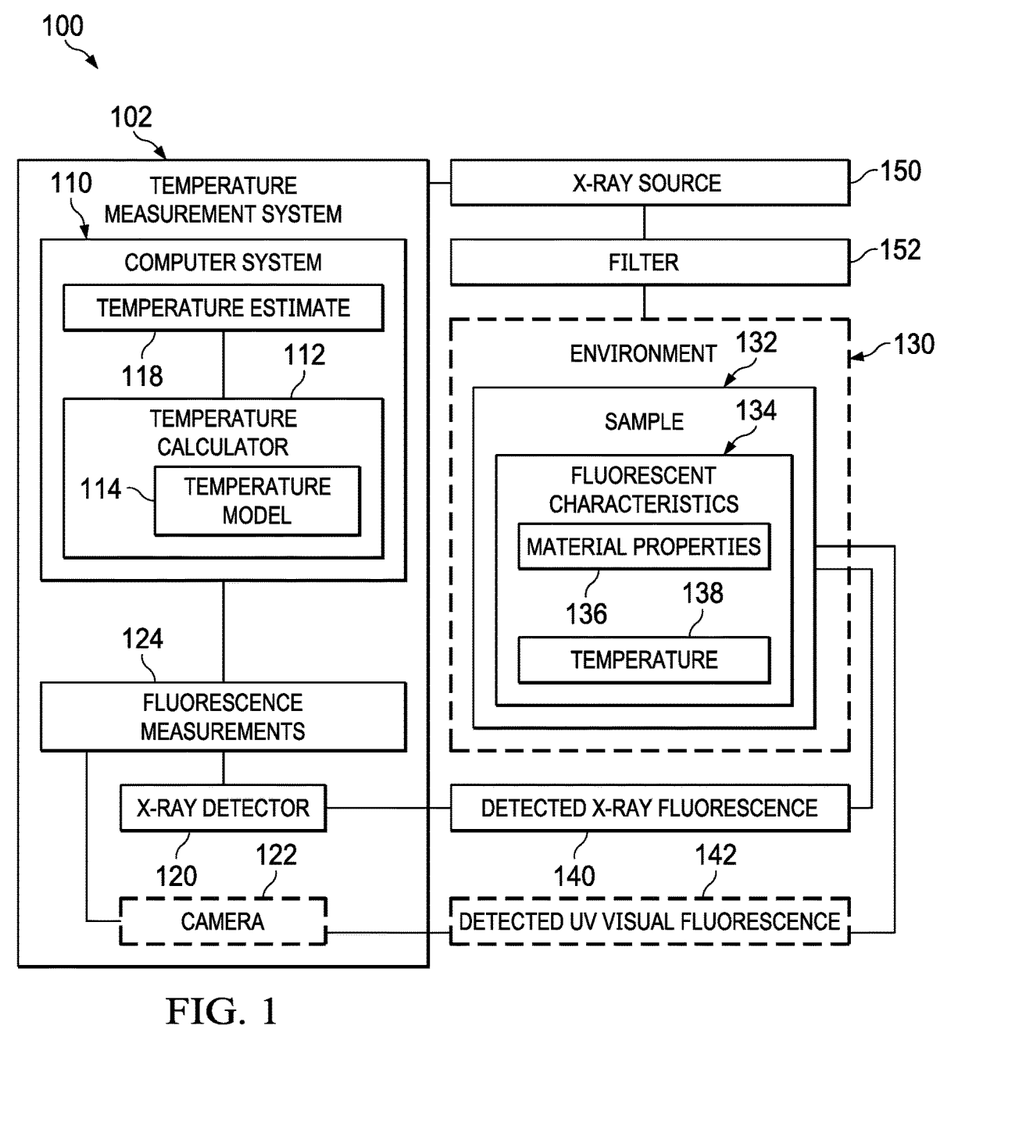
FIG. 1 depicts a block diagram of a system for sensing temperature using x-ray fluorescence in accordance with an illustrative embodiment.

Turning to FIG. 1, a block diagram of a system for sensing temperature using x-ray fluorescence is depicted in accordance with an illustrative embodiment. The temperature sensing system 100 is configured to detect the temperature 134 of sample 132.

Optionally, sample 132 might be inside environment 130, which is optically and/or thermally opaque. Examples of an opaque environment include, without limitation, a container enclosing the sample or a sooty fire in a furnace.

Alternatively, the sample 132 itself might be opaque, such as, e.g., plasma spray, burning rocket propellant, explosives, nuclear fuel rods, and metal beams. In the case of an opaque sample 132, the goal might be to measure the interior temperature in order to accurately calculate average temperature of the sample instead of just the surface/exterior temperature, which could be significantly different from the interior.

Temperature determining system 102 comprises X-ray detector 120 and computer 110. Temperature determining system 102 might optionally comprise camera 122.

X-ray detector 120 can be configured to detect X-ray fluorescence 140 generated by irradiation of sample 132 by X-ray source 150. X-ray fluorescence 140 depends on fluorescent characteristic 134 of sample 132. Fluorescent characteristics 134 are influenced by the material properties 136 and temperature 138 of sample 132.

In an optional configuration, temperature determining system 102 also comprises camera 122, which detects visual and/or ultraviolet (UV) fluorescence from sample 132 resulting from x-ray irradiation by x-ray source 150. Camera 122 might be employed in configurations wherein the sample 132 is not enclosed in a container or is otherwise visible.

Information regarding detected fluorescence 140 and visual fluorescence 142 can be provided as fluorescence measurements 124 to computer 110.

Computer system 110 can be implemented using any appropriate information processing system. Computer system 110 can be configured using any appropriate hardware or hardware in combination with software to implement temperature calculator 112 and temperature estimate 118.

As x-ray source 150 irradiate sample 132, the sample 132 emits x-ray photos photons and possibly visible photons (explained below). The x-rays from x-ray source 150 might be attenuated by filter 152. Temperature calculator 112 uses a temperature model 114 to determine temperature estimate 118 of the sample 132 based on the fluorescence measurements 124 provided by x-ray detector 120 and camera 122. Temperature model 114 is derived from an empirically determined relationship between x-ray fluorescence and temperature.

The illustration of temperature sensing system 100 in FIG. 1 is not meant to imply physical or architectural limitations to the manner in which illustrative embodiments may be implemented. Other components, in addition to or in place of the ones illustrated, may be used. Some components may be optional. Also, the blocks are presented to illustrate some functional components. One or more of these blocks may be combined, divided, or combined and divided into different blocks when implemented in an illustrative embodiment.

Figure 2:
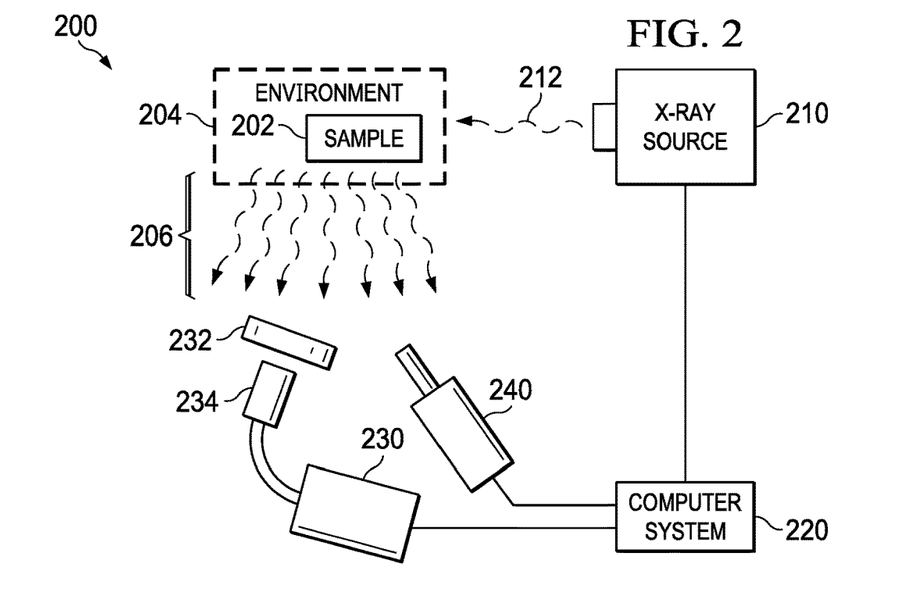
FIG. 2 depicts a diagram of an x-ray fluorescence temperature sensing system in accordance with illustrative embodiments.

FIG. 2 depicts a diagram of an x-ray fluorescence temperature sensing system in accordance with illustrative embodiments. System 200 might be an example implementation of temperature sensing system 100 in FIG. 1.

X-ray source 210 is arranged irradiate sample 202 with x-rays 212. X-ray source 210 can be, e.g., a standard laboratory x-ray machine or synchrotron radiation. In an illustrative embodiment, x-rays 212 are high-flux and move from the source 210 towards the sample 202. A laboratory machine emits a cone shaped beam while a synchrotron emits a parallel beam.

Sample 202 might comprise a thermographic material. In the example shown in FIG. 2, sample 202 might optionally be enclosed in an opaque environment 204 such as a container or sooty fire. Alternatively, sample 202 itself might be opaque as explained above (e.g., plasma spray). In response to irradiation by x-rays 212, the sample 202 emits photons 206, which are characteristic of the material comprising the sample 202.

Photons 206 might include x-ray photons, which are detected by x-ray detector 240. Photons 206 might also comprise photons in the visible spectrum, which are focused by focusing optics 232 for fiber optic detector 234 connected to camera 230. The use of camera 230 will depend on if the material characteristics of sample 202 are known to produce visual fluorescence in response to x-ray irradiation, as well as whether or not sample 202 is visible (e.g., not enclosed in an opaque container).

Measurements from x-ray detector 240 and optional camera 230 are fed to computer system 220. Using known fluorescent characteristics of the sample material, computer system 220 extrapolates the temperature of the sample 202 based on photon intensity as shown in FIG. 3.

Figure 3:
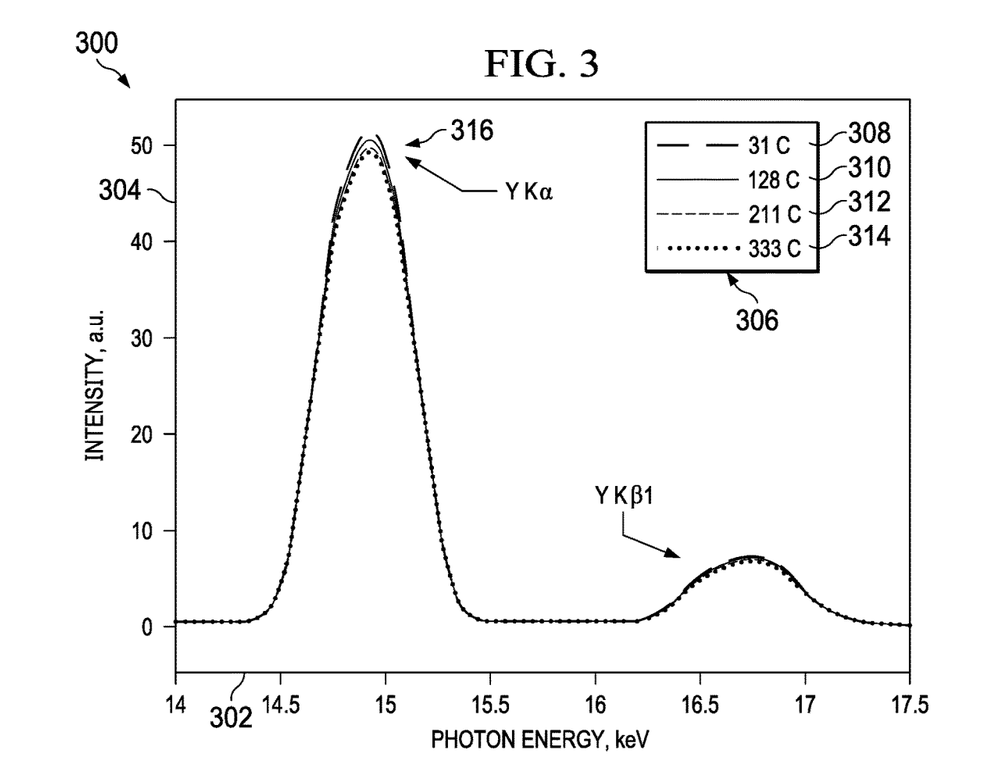
FIG. 3 depicts an x-ray spectral chart of different emission lines according to sample temperature in accordance with illustrative embodiments.

FIG. 3 depicts an x-ray spectral chart of different emission lines according to sample temperature in accordance with illustrative embodiments. Chart 300 comprises an x axis 302 representing photon energy and a y axis 304 representing photon intensity. In the present example, chart 300 illustrates the normalized x-ray spectrum of yttrium aluminum garnet ($Y_3Al_5O_{12}$) at four different temperatures: 31° C. 308, 128° C. 310, 211° C. 312, and 333° C. 314 as noted in legend 306.

As shown in FIG. 3, the peak 316 in photon intensity Y Kα is sensitive to temperature, with the peak decreasing as the temperature of the material increases.

Figure 4:
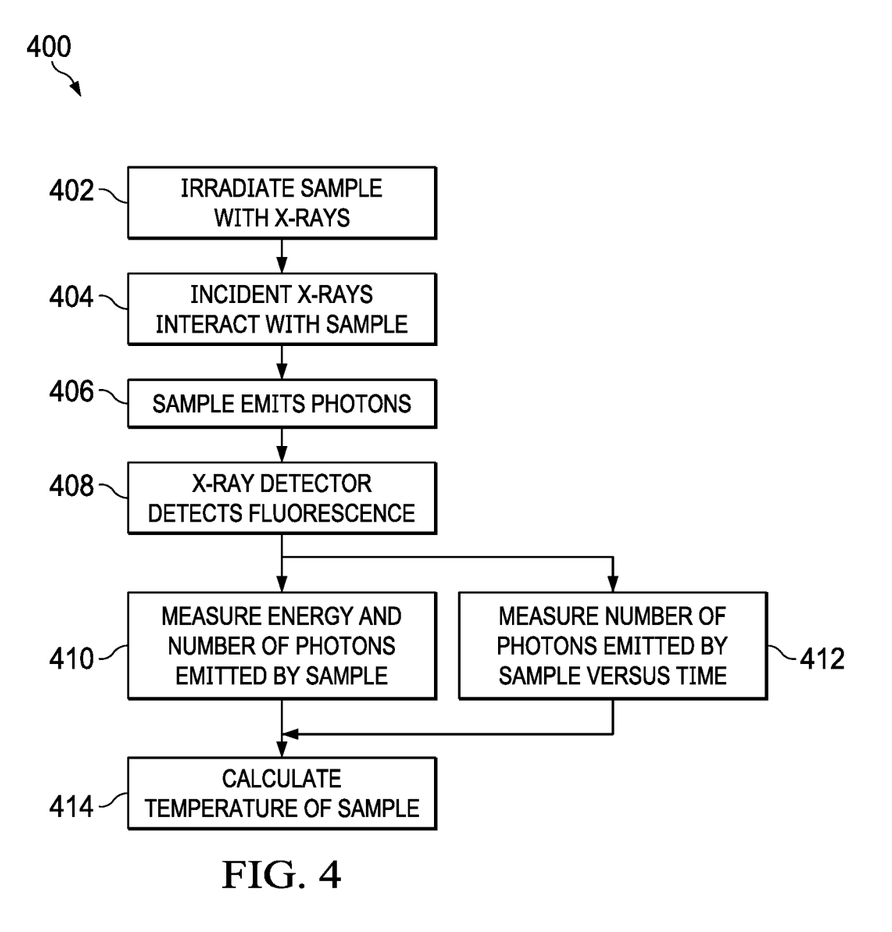
FIG. 4 is a flowchart depicting a process for determining temperature according to x-ray fluorescence in accordance with illustrative embodiments.

FIG. 4 is a flowchart depicting a process for determining temperature according to x-ray fluorescence in accordance with illustrative embodiments. Process 400 can be implement using temperature sensing system 100 shown in FIG. 1 and system 200 shown in FIG. 2.

Process 400 begins by irradiating a material sample with x-rays (step 402). The x-rays can be produced by a standard laboratory x-ray machine or synchrotron radiation. As described above, these are high-flux and moving from the source towards the thermographic material comprising the sample. X-ray energies can be emitted over a large range of eVs (bremsstrahlung) or be monochromatic. In an embodiment the peak x-ray energy from the source should be greater than the x-ray emission lines (characteristic x-rays) of the thermographic material in the sample.

Incident ex-rays interact with the sample according to the specific material properties of the sample (step 404). Depending on the sample material, most the x-rays are scattered, absorbed, or attenuated as they interact with the sample. There are three possible types of scattering/absorption interactions. In the first type, the primary photon is redirected without energy transfer (Rayleigh Scattering). In the second type of interaction, the primary photon is redirected with energy transfer to electron (Compton Scattering). The third type of interaction comprises ejection of an electron from an atom (Photo-Electric Effect). The illustrative embodiments take advantage of this third type of interaction.

In response, the sample emits photons (step 406). After an electron is ejected from an atom via the photo-electric effect, another electron will take its place by moving to a lower energy state (a position closer to the core of the atom). This transition from a higher energy state to a lower energy state creates a secondary photon whose energy is characteristic of the atom in the material creating it. This process continues, creating lower and lower energy electrons (x-rays, then UV light, visible light, etc.) until all the energy of the primary photon is dissipated through photon emissions, phonons, or thermal losses.

The x-ray detector detects the x-ray fluorescence of the sample (step 408) and performs two measurements.

The x-ray detector measures the energy and number of x-ray photons emitted by the sample (wavelength method) (step 410). X-ray detector measures the number of x-ray photons emitted by the sample versus time (time-decay method) (step 412).

Using these measurements and data processing, the computer system calculates the temperature of the sample (step 414).

Figure 5:
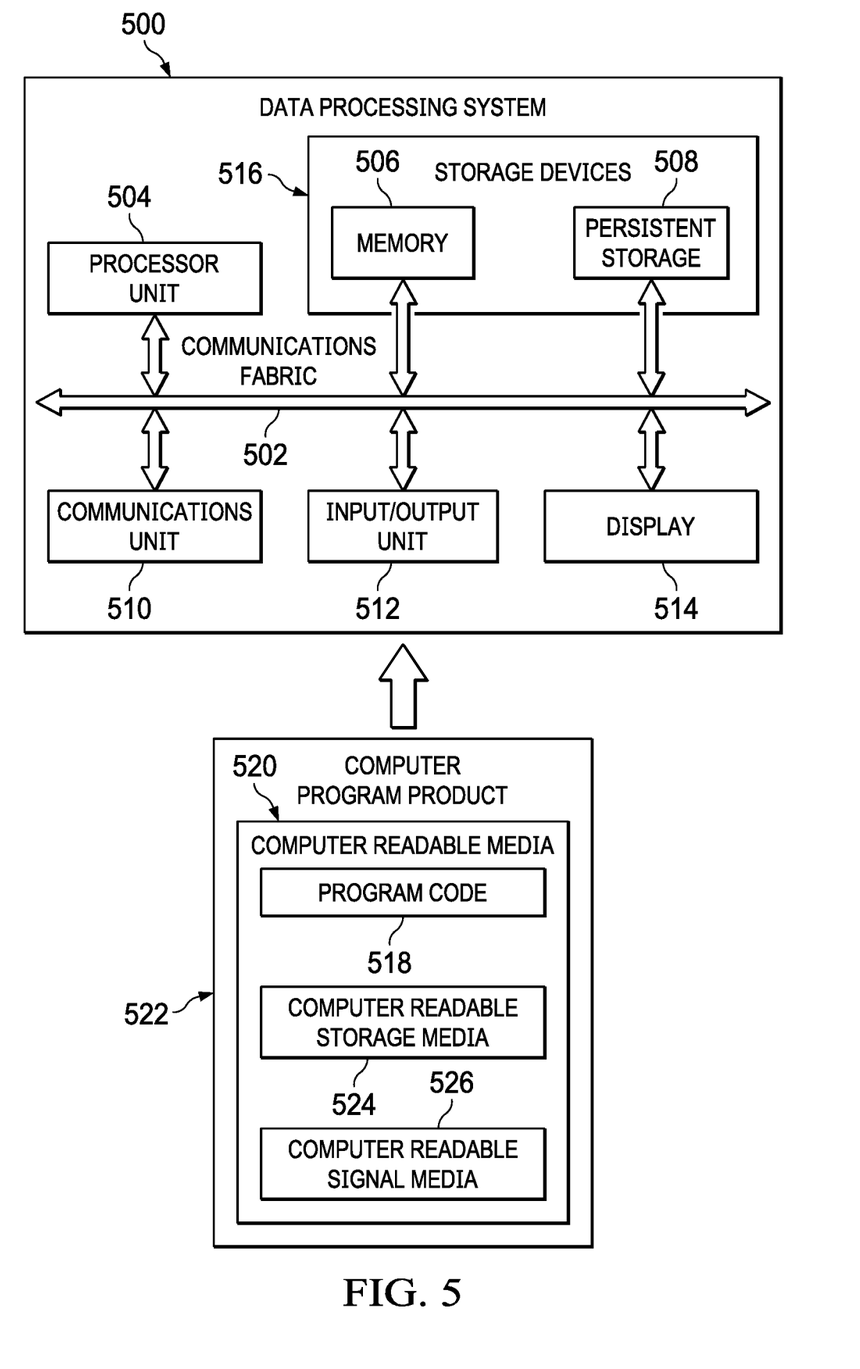
FIG. 5 is a diagram of a data processing system depicted in accordance with an illustrative embodiment.

Turning to FIG. 5, a diagram of a data processing system is depicted in accordance with an illustrative embodiment. Data processing system 500 is an example of a system in which computer-readable program code or program instructions implementing processes of illustrative embodiments may be run and can be an example of computer 110 in FIG. 1. In this illustrative example, data processing system 500 includes communications fabric 502, which provides communications between processor unit 504, memory 506, persistent storage 508, communications unit 510, input/output unit 512, and display 514.

Processor unit 504 serves to execute instructions for software applications and programs that may be loaded into memory 506. Processor unit 504 may be a set of one or more hardware processor devices or may be a multi-processor core, depending on the particular implementation. Further, processor unit 504 may be implemented using one or more heterogeneous processor systems, in which a main processor is present with secondary processors on a single chip. As another illustrative example, processor unit 504 may be a symmetric multi-processor system containing multiple processors of the same type.

A computer-readable storage device is any piece of hardware that is capable of storing information, such as, for example, without limitation, data, computer-readable program code in functional form, and/or other suitable information either on a transient basis and/or a persistent basis. Further, a computer-readable storage device excludes a propagation medium. Memory 506, in these examples, may be, for example, a random access memory, or any other suitable volatile or non-volatile storage device. Persistent storage 508 may take various forms, depending on the particular implementation. For example, persistent storage 508 may contain one or more devices. For example, persistent storage 508 may be a hard drive, a flash memory, a rewritable optical disk, a rewritable magnetic tape, or some combination of the above. The media used by persistent storage 508 may be removable. For example, a removable hard drive may be used for persistent storage 508.

Communications unit 510, in this example, provides for communication with other computers, data processing systems, and devices via network communications unit 510 may provide communications using both physical and wireless communications links. The physical communications link may utilize, for example, a wire, cable, universal serial bus, or any other physical technology to establish a physical communications link for data processing system 500. The wireless communications link may utilize, for example, shortwave, high frequency, ultra-high frequency, microwave, wireless fidelity (WiFi), Bluetooth technology, global system for mobile communications (GSM), code division multiple access (CDMA), second-generation (2G), third-generation (3G), fourth-generation (4G), 4G Long Term Evolution (LTE), LTE Advanced, or any other wireless communication technology or standard to establish a wireless communications link for data processing system 500.

Input/output unit 512 allows for the input and output of data with other devices that may be connected to data processing system 500. For example, input/output unit 512 may provide a connection for user input through a keypad, keyboard, and/or some other suitable input device. Display 514 provides a mechanism to display information to a user and may include touch screen capabilities to allow the user to make on-screen selections through user interfaces or input data, for example.

Instructions for the operating system, applications, and/or programs may be located in storage devices 516, which are in communication with processor unit 504 through communications fabric 502. In this illustrative example, the instructions are in a functional form on persistent storage 508. These instructions may be loaded into memory 506 for running by processor unit 504. The processes of the different embodiments may be performed by processor unit 504 using computer-implemented program instructions, which may be located in a memory, such as memory 506. These program instructions are referred to as program code, computer-usable program code, or computer-readable program code that may be read and run by a processor in processor unit 504. The program code, in the different embodiments, may be embodied on different physical computer-readable storage devices, such as memory 506 or persistent storage 508.

Program code 518 is located in a functional form on computer-readable media 520 that is selectively removable and may be loaded onto or transferred to data processing system 500 for running by processor unit 504. Program code 518 and computer-readable media 520 form computer program product 522. In one example, computer-readable media 520 may be computer-readable storage media 524 or computer-readable signal media 526. Computer-readable storage media 524 may include, for example, an optical or magnetic disc that is inserted or placed into a drive or other device that is part of persistent storage 508 for transfer onto a storage device, such as a hard drive, that is part of persistent storage 508. Computer-readable storage media 524 also may take the form of a persistent storage, such as a hard drive, a thumb drive, or a flash memory that is connected to data processing system 500. In some instances, computer-readable storage media 524 may not be removable from data processing system 500.

Alternatively, program code 518 may be transferred to data processing system 500 using computer-readable signal media 526. Computer-readable signal media 526 may be, for example, a propagated data signal containing program code 518. For example, computer-readable signal media 526 may be an electro-magnetic signal, an optical signal, and/or any other suitable type of signal. These signals may be transmitted over communication links, such as wireless communication links, an optical fiber cable, a coaxial cable, a wire, and/or any other suitable type of communications link. In other words, the communications link and/or the connection may be physical or wireless in the illustrative examples. The computer-readable media also may take the form of non-tangible media, such as communication links or wireless transmissions containing the program code.

In some illustrative embodiments, program code 518 may be downloaded over a network to persistent storage 508 from another device or data processing system through computer-readable signal media 526 for use within data processing system 500. For instance, program code stored in a computer-readable storage media in a data processing system may be downloaded over a network from the data processing system to data processing system 500. The data processing system providing program code 518 may be a server computer, a client computer, or some other device capable of storing and transmitting program code 518.

The different components illustrated for data processing system 500 are not meant to provide architectural limitations to the manner in which different embodiments may be implemented. The different illustrative embodiments may be implemented in a data processing system including components in addition to, or in place of, those illustrated for data processing system 500. Other components shown in FIG. 5 can be varied from the illustrative examples shown. The different embodiments may be implemented using any hardware device or system capable of executing program code. As one example, data processing system 500 may include organic components integrated with inorganic components and/or may be comprised entirely of organic components excluding a human being. For example, a storage device may be comprised of an organic semiconductor.

As another example, a computer-readable storage device in data processing system 500 is any hardware apparatus that may store data. Memory 506, persistent storage 508, and computer-readable storage media 524 are examples of physical storage devices in a tangible form.

In another example, a bus system may be used to implement communications fabric 502 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 506 or a cache such as found in an interface and memory controller hub that may be present in communications fabric 502.

The present invention may be a system, a method, and/or a computer program product. The computer program product may include a computer-readable storage medium or media having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as C++ or the like, and conventional procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer-readable program instructions by utilizing state information of the computer readable program instructions to personalize the electronic circuitry, in order to perform aspects of the present invention.

The flowchart and block diagrams in the different depicted embodiments illustrate the architecture, functionality, and operation of some possible implementations of apparatuses and methods in an illustrative embodiment. In this regard, each block in the flowchart or block diagrams may represent at least one of a module, a segment, a function, or a portion of an operation or step. For example, one or more of the blocks may be implemented as program code, hardware, or a combination of the program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware. Each block in the flowchart or the block diagrams may be implemented using special purpose hardware systems that perform the different operations or combinations of special purpose hardware and program code run by the special purpose hardware. Some steps of the process may be implemented by an additive manufacturing machine such as, for example, a 3D printer.

In some alternative implementations of an illustrative embodiment, the function or functions noted in the blocks may occur out of the order noted in the figure. For example, in some cases, two blocks shown in succession may be performed substantially concurrently, or the blocks may sometimes be performed in the reverse order, depending upon the functionality involved. Also, other blocks may be added in addition to the illustrated blocks in a flowchart or block diagram.

Detailed embodiments of the claimed structures and methods are disclosed herein; however, it is to be understood that the disclosed embodiments are merely illustrative of the claimed structures and methods that may be embodied in various forms. In addition, each of the examples given in connection with the various embodiments is intended to be illustrative, and not restrictive.

Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the methods and structures of the present disclosure.

As used herein, the phrase "a number" means one or more. The phrase "at least one of", when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, without limitation, "at least one of item A, item B, or item C" may include item A, item A and item B, or item C. This example also may include item A, item B, and item C or item B and item C. Of course, any combinations of these items may be present. In some illustrative examples, "at least one of" may be, for example, without limitation, two of item A; one of item B; and ten of item C; four of item B and seven of item C; or other suitable combinations.

For purposes of the description hereinafter, the terms "upper," "lower," "right," "left," "vertical," "horizontal," "top," "bottom," and derivatives thereof shall relate to the embodiments of the disclosure, as it is oriented in the drawing figures. The terms "positioned on" means that a first element, such as a first structure, is present on a second element, such as a second structure, wherein intervening elements, such as an interface structure, e.g. interface layer, may be present between the first element and the second element.

In this disclosure, when an element, such as a layer, region, or substrate is referred to as being "on" or "over" another element, the element can be directly on the other element or intervening elements can also be present. In contrast, when an element is referred to as being "directly on," "directly over," or "on and in direct contact with" another element, there are no intervening elements present, and the element is in contact with another element.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiment. The terminology used herein was chosen to best explain the principles of the embodiment, the practical application or technical improvement over technologies found in the marketplace, or to enable others of ordinary skill in the art to understand the embodiments disclosed here.

What is claimed is:

1. A method of determining temperature, the method comprising:
   irradiating, by an x-ray source, a sample of a material with x-rays;
   detecting, by a number of photon detectors, photon fluorescence produced by the sample in response to the x-ray irradiation; and
   determining, by a number of processors, a temperature of the sample according to a predetermined relationship between photon fluorescence and temperature for the material.

2. The method of claim 1, wherein the sample comprises a thermographic material.

3. The method of claim 1, wherein photon fluorescence produced by the sample is x-ray fluorescence.

4. The method of claim 1, wherein photon fluorescence produced by the sample is visual fluorescence.

5. The method of claim 1, wherein the sample is in an opaque environment.

6. The method of claim 5, wherein the sample is enclosed in a container.

7. The method of claim 1, wherein the sample is opaque.

8. The method of claim 1, wherein the photon detectors comprise x-ray detectors.

9. The method of claim 8, wherein the x-ray detectors measure energy and number of x-ray photons emitted by the sample.

10. The method of claim 8, wherein the x-ray detectors measure number of x-ray photons emitted by the sample versus time.

11. The method of claim 1, wherein the photon detectors comprise cameras.

12. A system for determining temperature, the system comprising:
   an x-ray source;
   a number of photon detectors;
   a number of processors in communication with the x-ray source and photon detectors, wherein the number of processors are configured to execute program instructions to:
      irradiate, with the x-ray source, a sample of a material;
      detect, with the photon detectors, photon fluorescence produced by the sample in response to the x-ray irradiation; and
      determining a temperature of the sample according to a predetermined relationship between photon fluorescence and temperature for the material.

13. The system of claim 12, wherein photon fluorescence produced by the sample is x-ray fluorescence.

14. The system of claim 12, wherein photon fluorescence produced by the sample is visual fluorescence.

15. The system of claim 12, wherein the sample is in an opaque environment.

16. The system of claim 15, wherein the sample is enclosed in a container.

17. The system of claim 12, wherein the sample is opaque.

18. The system of claim 12, wherein the photon detectors comprise x-ray detectors.

19. The system of claim 18, wherein the x-ray detectors are configured to measure energy and number of x-ray photons emitted by the sample.

20. The system of claim 18, wherein the x-ray detectors measure number of x-ray photons emitted by the sample versus time.

21. The method of claim 12, wherein the photon detectors comprise cameras.

* * * * *